US008296172B2

(12) United States Patent
Marci et al.

(10) Patent No.: US 8,296,172 B2
(45) Date of Patent: Oct. 23, 2012

(54) METHOD AND SYSTEM FOR DETERMINING AUDIENCE RESPONSE TO A SENSORY STIMULUS

(75) Inventors: Carl D. Marci, Boston, MA (US); Brian Levine, Arlington, MA (US)

(73) Assignee: Innerscope Research, Inc., Boston, MA (US)

( * ) Notice: Subject to any disclaimer, the term of this patent is extended or adjusted under 35 U.S.C. 154(b) by 878 days.

(21) Appl. No.: 11/850,650

(22) Filed: Sep. 5, 2007

(65) Prior Publication Data

US 2008/0091512 A1    Apr. 17, 2008

Related U.S. Application Data

(60) Provisional application No. 60/824,546, filed on Sep. 5, 2006.

(51) Int. Cl.
 *G06Q 10/00* (2012.01)
(52) U.S. Cl. .................................................. 705/7.29
(58) Field of Classification Search .................. 705/7.29
See application file for complete search history.

(56) References Cited

U.S. PATENT DOCUMENTS

| | | | | |
|---|---|---|---|---|
| 5,243,517 | A | | 9/1993 | Schmidt et al. ............. 364/419.2 |
| 5,436,830 | A | | 7/1995 | Zatlman ...................... 364/419.2 |
| 5,676,138 | A | * | 10/1997 | Zawilinski ..................... 600/301 |
| 5,676,148 | A | | 10/1997 | Koo et al. .................. 128/661.01 |
| 6,099,319 | A | | 8/2000 | Zaltman et al. ............... 434/236 |
| 6,315,569 | B1 | | 11/2001 | Zaltman ......................... 434/236 |
| 6,358,201 | B1 | | 3/2002 | Childre et al. ................. 600/300 |
| 6,422,999 | B1 | | 7/2002 | Hill .............................. 600/300 |
| 6,453,241 | B1 | * | 9/2002 | Bassett et al. .................... 702/19 |
| 6,850,252 | B1 | | 2/2005 | Hoffberg ....................... 345/716 |
| 6,852,875 | B2 | | 2/2005 | Prakash .......................... 560/40 |
| 7,930,199 | B1 | | 4/2011 | Hill .............................. 705/7.29 |
| 2002/0059577 | A1 | | 5/2002 | Lu et al. ........................... 725/9 |
| 2003/0063222 | A1 | | 4/2003 | Creed et al. .................. 348/687 |
| 2003/0149344 | A1 | | 8/2003 | Nizan .......................... 600/300 |

(Continued)

FOREIGN PATENT DOCUMENTS

JP         2001-147944         5/2001

(Continued)

OTHER PUBLICATIONS

"ARF, AAAA and ANA Are Getting Emotional about Engagement", Presentation, pp. 1-103 (2005).

(Continued)

*Primary Examiner* — Johnna Loftis
*Assistant Examiner* — Brandi P Parker
(74) *Attorney, Agent, or Firm* — Murphy & King, P.C.

(57) ABSTRACT

The present invention is directed to a method and system for measuring the biologically based responses of an audience to a presentation that provides sensory stimulating experience and determining a measure of the level and pattern of engagement of that audience to the presentation. In particular, the invention is directed to a method and system for measuring one or more biologically based responses of one or more persons being exposed to the presentation in order to determine the moment-to-moment pattern and overall level of engagement. Further, the invention can be used to determine whether the presentation or the content in the presentation is more effective in a population relative to other presentations (or content) and other populations and to help identify elements of the presentation that contribute to the high level of engagement and the effectiveness and success of the presentation for that population.

19 Claims, 7 Drawing Sheets

U.S. PATENT DOCUMENTS

| | | | |
|---|---|---|---|
| 2004/0133081 A1 | 7/2004 | Teller et al. | 600/300 |
| 2004/0219184 A1* | 11/2004 | Brown et al. | 424/423 |
| 2005/0060312 A1 | 3/2005 | Curtiss et al. | 707/7 |
| 2005/0062637 A1 | 3/2005 | El Zabadani et al. | 341/176 |
| 2005/0071462 A1 | 3/2005 | Bodin et al. | 709/224 |
| 2005/0071865 A1 | 3/2005 | Martins | 725/10 |
| 2006/0129458 A1* | 6/2006 | Maggio | 705/14 |
| 2007/0038516 A1 | 2/2007 | Apple et al. | |
| 2008/0091512 A1 | 4/2008 | Marci et al. | |
| 2008/0255949 A1 | 10/2008 | Genco et al. | |

FOREIGN PATENT DOCUMENTS

| | | |
|---|---|---|
| JP | 2005-51654 | 2/2005 |
| JP | 2006-227994 | 8/2006 |
| JP | 2006-6355 | 7/2007 |

OTHER PUBLICATIONS

Boltz, M.G., "The cognitive processing of film and musical soundtracks", *Memory & Cognition*, 32(7):1194-1205 (2004).

Christie et al., "Autonomic specificity of discrete emotion and dimensions of affective space: a multivariate approach", *Int'l J. Psychophysiol.*, 51:143-153 (2004).

Coombes et al., "Emotion and movement: Activation of defensive circuitry alters the magnitude of a sustained muscle contraction", *Neurosci. Lett.*, 396:192-196 (2006).

Cryer et al., "Pull the plug on stress", *Harv. Bus. Rev.*, 81(7):102-107 (2003).

Demaree et al., "Predicting facial valence to negative stimuli from resting RSA: Not a function of active emotion regulation", *Cognition and Emotion*, 20(2):161-176 (2006).

Ekman et al., "Autonomic Nervous System Activity Distinguishes among Emotions", *Science*, 221(4616):1208-1210 (1983).

Elton, C., "Measuring emotion at the symphony", http://www.boston.com, pp. 1-3 (2006).

Goldberg, C., "Getting wired could help predict emotions", http://www.boston.com, pp. 1-4 (2005).

Gomez et al., "Respiratory responses associated with affective processing of film stimuli", *Biol. Psychol.*, 68:223-235 (2005).

Hall, B.F., "A New Approach to Measuring Advertising Effectiveness", Article 1502a:1-17 (2001).

Hall, B.F., "Advertising as a factor of production", *Admap*, pp. 30-32 (2003).

Hall, B.F., "Is cognitive processing the right dimension", *Admap*, pp. 37-39 (2003).

Hall, B.F., "On Measuring the Power Communications", *JAR*, pp. 1-11 (2004).

Hall, B.F., "Research and strategy: a fall from grace", *Admap*, pp. 2-4 (2003).

Hall, B.F., "Review of Casting for Big Ideas, by Andrew Jaffe", pp. 1-2 (2003).

Hall, B.F., "Why Advertisers Do It", pp. 1-5 (2003).

Hubert et al., "Autonomic, neuroendocrine, and subjective responses to emotion-inducing film stimuli", *Int'l J. Psychophysiol.*, 11:131-140 (1991).

Levenson et al., "Emotion and Autonomic Nervous System Activity in the Minangkabau of West Sumatra", *J. Personality Soc. Psychol.*, 62(6):972-988 (1992).

Marci et al., "The Effect of Emotional Distance on Pyschophysiologic Concordance and Perceived Empathy Between Patient and Interviewer", *Appl. Psychophysiol. Biofeedback*, 31:115-129 (2006).

McCraty et al., "Analysis of twenty-four hour heart rate variability in patients with panic disorder", *Biol. Psychol.*, 56(2):131-150 (2001).

McCraty et al., "Electrophysiolocial Evidence of Intuition: Part 1. The Surprising Role of the Heart", *J. Altern. Complement. Med.*, 10(1):133-143 (2004).

McCraty et al., "Electrophysiological evidence of intuition: Part 2. A system-wide process?", *J. Altern. Complement. Med.*, 10(2\0):325-336 (2004).

McCraty et al., "Impact of a Workplace Stress Reduction Program on Blood Pressure and Emotional Health in Hypertensive Employees", *J. Altern. Complement. Med.*, 9(3):355-369 (2003).

McCraty et al., "The Effects of Different Types of Music on Mood, Tension, and Mental Clarity", *Altern. Ther. Health Med.*, 4(1):75-84 (1998).

McCarty et al., "The Effects of Emotions on Ahort-Term Power Spectrum Analysis of Heart Rate Variability", *Am. J. Cardiol.*, 76(14):1089-1093 (1995).

McCraty et al., "The Impact of a New Emotional Self-Management Program on Stress, Emotions, Heart Rate Variability, DHEA and Cortisol", *Intergr. Physiol. Behav. Sci.*, 33(2):151-170 (1998).

McCraty et al., "The Impact of an Emotional Self-Management Skills Course on Psychosocial Functioning and Autonomic Recovery to Stress in Middle School Children", *Integr. Physiol. Behav. Sci.*, 34(4):246-268 (1999).

Melillo, W., "Inside the consumer mind: What Neuroscience can tell us about marketing", http://www.answerstream.com, pp. 1-13 (2006).

Miller et al., "Influence of Specific Emotional States on Autonomic Reactivity and Pulmonary Function in Asthmatic Children", *J. Am. Acad. Child Adolescent Psychiatry*, 36(5):669-677 (1997).

Murphy et al., "The Heart Reinnervates After Transplantation", *Ann. Thorac. Surg.*, 69(6):1769-1781 (2000).

Ranii, D., "Adding Science to Gut Check", *The News & Observer*, pp. 1 (2005).

Rosenberg, K., "Emotional R.O.I.", *The Hub*, pp. 24-25 (2006).

Tiller et al., "Cardiac Coherence: A New, Noninvasive Measure of Autonomic Nervous System Order", *Altern. Ther. Health Med.*, 2(1):52-65 (1996).

"Topline: Emotional Response to Advertising", *MSW Research*, pp. 1-6 (2005).

Umetani et al., "Twenty-Four Hour Time Domain Heart Rate Variability and Heart Rate: Relations to Age and Gender Over Nine Decades", *j. Am. Coll. Cardiol.*, 31(3):593-601 (1998).

Von Leupoldt et al., "Emotions in a Body Plethysmograph", *J. Psychophysiol.*, 18(4):170-176 (2004).

International Search Report dated Nov. 9, 2010 of corresponding International Patent Application No. PCT/US2010/031375.

Australian Office Action dated Mar. 26, 2012 of corresponding Australian Patent Application No. 2007293092.

Japanese Office Action dated Apr. 25, 2012 of corresponding Japanese Patent Application No. 2009-527401.

Non-Final Office Action dated Apr. 25, 2012 of corresponding U.S. Appl. No. 12/426,259.

* cited by examiner

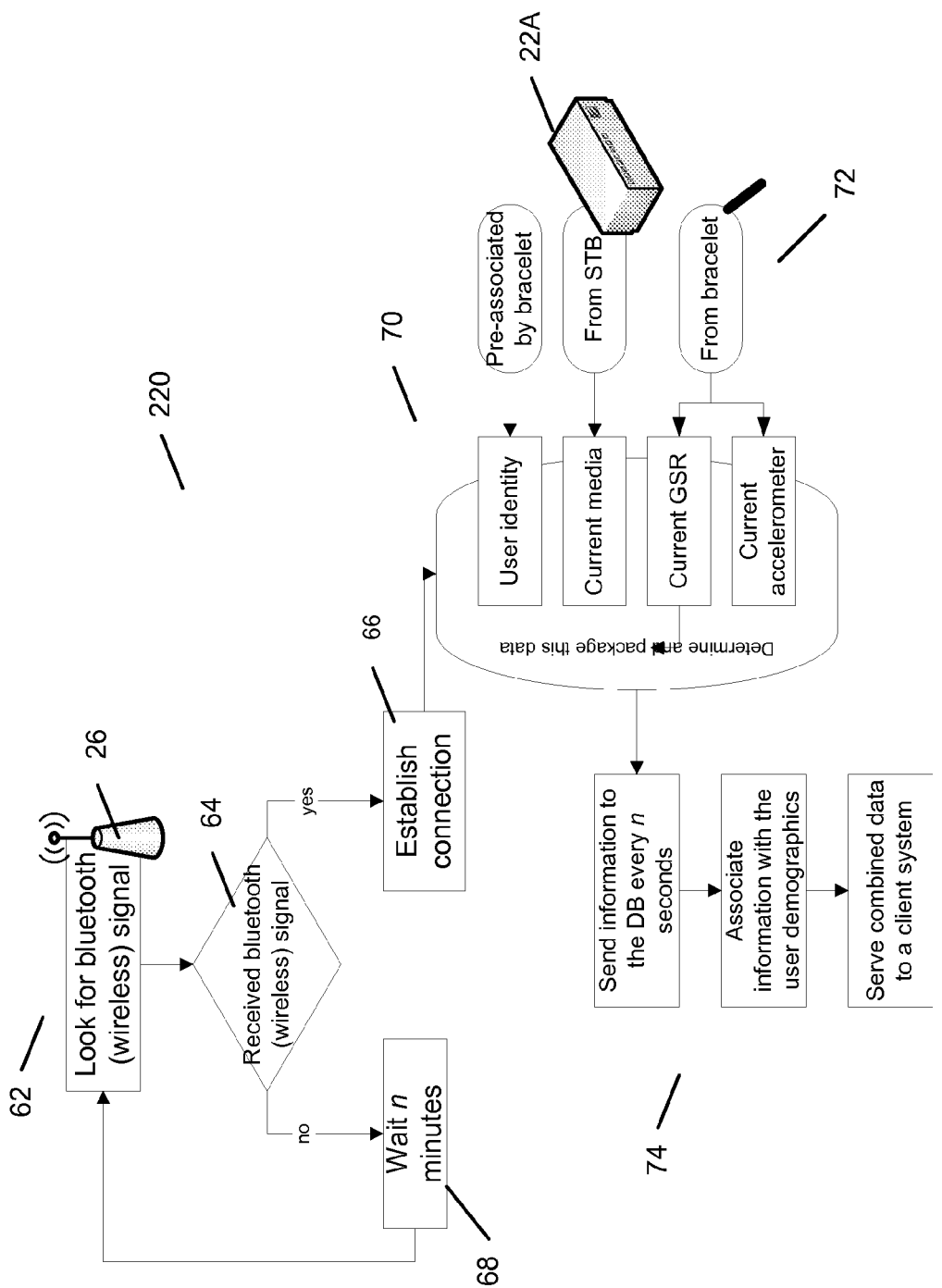

METHOD AND SYSTEM FOR DETERMINING AUDIENCE RESPONSE TO A SENSORY STIMULUS

CROSS-REFERENCE TO RELATED APPLICATIONS

This application claims any and all benefits as provided by law of U.S. Provisional Application No. 60/824,546 filed Sep. 5, 2006 which is hereby incorporated by reference in its entirety.

STATEMENT REGARDING FEDERALLY SPONSORED RESEARCH

Not Applicable

REFERENCE TO MICROFICHE APPENDIX

Not Applicable

BACKGROUND

The present invention is directed to a method and system for exposing a sample population audience to a presentation (a sensory stimulus) and evaluating the audience's experience by measuring the biologically based responses of the audience to the presentation and determining a measure of the level and pattern of intensity, synchrony and engagement of that audience to the presentation.

There are many different kinds of audio, visual and audio-visual presentations that people are exposed to every day. These presentations serve as sensory experiences that stimulate our senses and are known to result in biologically based responses that can be measured electronically and mechanically (for example, heart rate, respiration rate, blood pressure, and skin conductance).

A commonly used approach in making measurements for evaluating these presentations is that of interrogation, wherein the television/media viewer and/or Internet user and/or game player is asked to identify himself or herself as a member of the television/media audience or as an Internet user or as a game player. In connection with television viewing, this inquiry is usually done by means of an electronic prompting and data input device (for example, as in a Portable People Meter by Arbitron, Inc.) associated with a monitored receiver in a statistically selected population and monitoring site. The member identification may also include age, sex, and other demographic data. It is common to store both the demographic data and the tuning data associated with each monitored receiver in the statistically selected monitoring site in store-and-forward equipment located within the monitoring site and to subsequently forward these data to a central office computer via a direct call over the public switched telephone network, or via the Internet, on a regular basis.

These non-biologically based self-report methods of measuring audience response are known to be highly error prone. Personal logs are subjective resulting in recall biases, home monitoring devices require event-recording by the person and suffer low compliance, while digital monitoring of cable and internet signals cannot identify which household member or members are in the audience nor can they evaluate the level of responsiveness by those members. In addition, self-report offers no ability to capture the biological responses to a media presentation. Thus, while methods of self-report offer valuable data, they are highly error prone and cannot track the moment-to-moment responses to media consumption.

SUMMARY

Historically, biologically based testing focuses on using one or two physiological responses (e.g., heart rate or electroencephaolography) to determining the specific emotion elicited in response to a particular stimulus, such as advertising media, be it a photograph, a print ad, or a television commercial. However, determining the specific emotion elicited does not help to predict how these emotional responses lead to desired behavioral responses or changes in behavior. Further, this testing focuses on the responses of individuals. Thus, it is desirable to identify physiologically or biologically based responses or patterns of responses in a population sample that can lead to or are associated with behavioral responses or changes in behaviors of the target population.

The present invention relates to a system and method for use in the field of audience measurement. Specifically, the invention is directed to a method and system for recording the biologically based audience responses to a presentation (for example, a live or recorded, passive or interactive audio, visual, audio-visual presentation) and for determining a measure of moment-to-moment and overall intensity, synchrony and engagement of the audience with that stimulus presentation. The measure of engagement of the sample population audience can then be used to estimate the level to which a population as a whole will be engaged by, or like or dislike, the same presentation. The measure of engagement of the audience when combined with eye-tracking technology can also be used to determine what elements of a presentation are most engaging relative to other elements in that or a similar presentation. The measures of intensity, synchrony and engagement can be used both for diagnostic value and/or to anticipate the success or failure of a presentation. This can be accomplished via predictive models for comparing, for example, the measure of intensity, synchrony or engagement of known successful presentations to the measure of engagement for an unknown or not previously evaluated presentation for a sample population (representative audience).

The invention can be used as a media testing tool used in place of or as a complement to traditional dial testing, self-report surveys and focus groups to measure audience reaction. The invention can utilize human neurobiology and embodied responses that are measured and processed in accordance with the invention to measure a sample audience reaction and predict the response of a more general audience.

In accordance with one embodiment, a sample audience of 2 or more people is presented with a piece of content (live or pre-recorded) that can last anywhere from 5 seconds to 5 hours (or more). The system according to the invention monitors the biometric responses of our viewers to obtain an objective measure of their response to said content.

Biometric response data can be gathered via a multi-sensor wearable body monitoring device that enables continuous collection of biologically based data that is time-stamped in order to correlate it to the presentation. This sensor package can include a measure of skin conductivity (SC), and can include any number of additional sensors to monitor responses such as heart response, brain waves, respiratory response, body movements, eye tracking, facial expressions and other biologically based signals.

The content that is presented to the audience as part of the presentation can include, but is not limited to, photographs, print advertisements, television programs, films, documentaries, commercials, infomercials, news reports, live content, live theater, theater recordings, mock trials, story boards, actor auditions, television pilots and film concepts, music, the Internet, gaming, etc.

In accordance with the invention, the response data can be collected individually, in a small group, or large group environment and be noninvasive (all sensors can be external).

In accordance with the invention, the system can track what presentation is being viewed, who is viewing the content and the biological response(s) of the audience members in time-locked correspondence to the viewed content or presentation. Thus, for a given piece of content or a presentation being viewed, the biological response of each member of the sample population can be associated with a portion of the content and the data from more than one sample audience gathered at different times and places can be combined. For the purposes of this invention, the sample audience (or sample population) can be a single individual who is monitored viewing the same content several times, such as over the course of several days.

In one embodiment, a system according to the invention can help content creators, distributors and marketers gain an objective view of how their audiences will respond to their content.

In one embodiment, the system can be used in a natural home environment and be as noninvasive as possible. The system can track what television (and other media) is being viewed by household members, which members are viewing and exactly which segments those members are watching.

To members of the household, they can control their media in the same way as before. For them, the main difference is that they must wear a sensor device (for example, a special article of clothing, a bracelet or other device) as they watch video or listen to music. In this example, this device can be used to determine how engaged they are with the media being played by using biological sensors. The system can make assessments about the data collected, for example, the greater the level of movement, the less likely the audience member is paying attention and the more likely they are engaged in a non-passive viewing experience.

In one embodiment, the data collected by the device is only used if the device or the viewer is determined to be close to the media display; otherwise, it is assumed the viewer is too far away from the media to experience it. The data is transmitted to the set-top box (STB) or receiver at regular intervals and associated with each audience members' identification plus information about the current media being consumed. This data can be packaged together in a database and served in real time.

In one embodiment of the system, to address compliance issues, users will not be able to change the channel unless they are wearing a functioning sensor device or charging a discharged unit in the outlet/dock attached to the STB or receiver.

This system according to the invention can be used by presentation and content creators to evaluate their programming before widely distributing it. For example, they can use the system to evaluate a sample audience by "pushing" the video and audio they want evaluated directly to a sample audience member's home entertainment systems or computer.

These and other capabilities of the invention, along with the invention itself, will be more fully understood after a review of the following figures, detailed description, and claims.

BRIEF DESCRIPTION OF THE FIGURES

FIG. 2C is a flow diagram of one aspect of the in-home system, its ability to identify who in a given household is actually experiencing media.

DETAILED DESCRIPTION OF PREFERRED EMBODIMENTS

Figure 1:
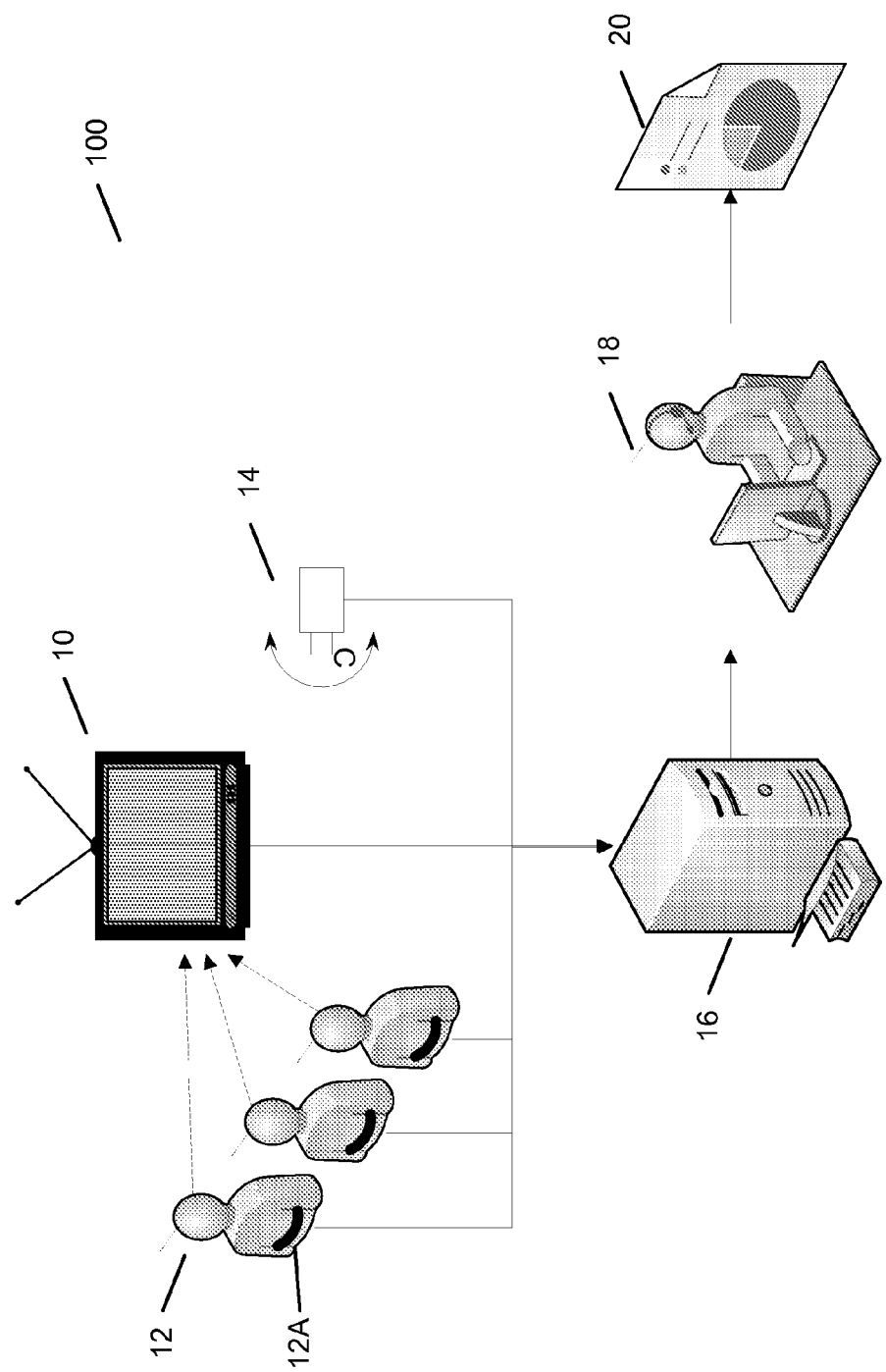
FIG. 1 is a schematic diagram of a system according to the invention for audience measurement in a test theater.

The present invention is directed to a method and system for determining a measure of a sample population's experience by measuring the biologically based responses of its members to a presentation that provides a sensory stimulating experience. Methods and systems according to the invention determine a measure of the level and pattern of intensity, synchrony and engagement of the sensory stimulating experience. In particular, the invention is directed to a method and system for measuring one or more biologically based responses of one or more persons being exposed to a sensory stimulus or presentation in order to determine the moment-to-moment pattern and overall level of engagement. Further, the invention can be used to determine whether the presentation is more effective with a population relative to other presentations and other populations and to help identify elements of the presentation that contribute to the high level of engagement and the effectiveness and success of the presentation.

There are many different kinds of audio, visual and audio-visual presentations that people are exposed to every day. These presentations serve as stimuli to our senses. Many of these presentations are designed to elicit responses. In some instances, an artist, musician or movie director has created a presentation that is intended to elicit one or more emotions or a series of responses from an audience. In other instances, the presentation is intended to educate or promote a product, a service, an organization, or a cause. Finally, there are often occasions and applications where the level of engagement of the audience is in response to a live person such as during a live performance, focus group, during an interview situation or any such social interaction.

These sensory stimuli can be in the form of a sound or a collection of sounds, a single picture or collection of pictures or an audio-visual presentation that is presented passively such as on television or radio, or presented in an interactive environment such as in a video game or internet experience. The sensory stimuli can be pre-recorded or presented live such as in a theatrical performance or legal proceeding (passive) or a real-world situation (or simulation) such as participating on a boat cruise or theme park ride (interactive).

Scientific research over the last two decades suggests that a person's responses to experiences are critical for the depth of processing of the content. The level of processing in turn affects the impact the content can have on the target audience and the ability to produce an attitudinal or behavioral change. Several studies even show that more arousing content leads to better recall of that content at a later date. This is of special interest to a variety of industry professionals including but not limited to creative directors, entertainment specialists, politicians and advertisers. For example, in the entertainment field, it is desirable to be able to assess which works are most appealing to which audiences (e.g., children, senior citizens, men and women). Not only would this information be useful to the creator and the promoter in identifying the target audience, but also to corporate sponsors and advertisers for advertising purposes. The ability to estimate the overall impact of a given stimulus is also important to clinicians trying to educate patients, teachers inspiring students, or politicians persuading constituents. Thus, it is desirable to determine which, if any, demographic groups will find a particular piece of media content to be engaging in order to help determine its impact. Similarly, it is desirable to determine which, if any, demographic groups find a particular print, internet, television or radio commercial engaging in order to ultimately have the ability to predict human behavior, such as attitudinal change, purchasing activity, or social conduct.

Biologically based responses to passive and interactive presentations can be measured using various sensors affixed to the body to record various biological responses including but not limited to heart rate, respiration rate, motion, and skin conductivity. There are now multiple products and new technologies on the market that allow continuous unobtrusive monitoring of biologically based human responses, for example, many are often employed for health and fitness purposes. One product, offered under the name LifeShirt System (VivoMetrics, Ventura Calif.) is a state-of-the-art garment that is worn unobtrusively by a person being evaluated and can simultaneously collect pulmonary, cardiac, skin, posture and vocal information for later analysis. Another product, offered under the name SenseWear (BodyMedia, Pittsburgh Pa.) is an arm-band that simultaneously collects skin conductance, body temperature, motion, and heart rate. Also, a product offered under the name Tobii x50 Eye Tracker or Tobii 2150 (Tobii Technology, McLean Va.) is a state-of-the-art eye-tracking device that allows for unobtrusive monitoring of eye fixation location and fixation duration to a high degree of certainty. By combining eye-tracking with other biologically based responses, the system can uniquely predict what specific elements within a complex sensory experience (e.g., multimedia or Internet experience) are triggering the response.

In accordance with the invention, a method and system has been proposed that can reliably and objectively quantify moment-to-moment patterns and overall responses to passive and interactive audio, video, and audio-video content in a target audience as a whole. Rather than use individual biological responses to identify individual emotions in individual participants, the present invention is directed to methods and systems that can aggregate biologically based responses of a representative sample population of a target audience to create a moment-to-moment and overall index of engagement of the target audience with respect to a presentation that provides a sensory stimulating experience.

The present invention is directed to a method and system for collecting data representative of various biologically based responses of a person (or animal) to an audio, visual or audio-visual presentation that provides a sensory stimulating experience, such as a sound or sequence of sounds, a picture or a sequence of pictures including video, or a combination of one or more sounds and one or more pictures, including video. The presentation can be pre-recorded and played back on a presentation device or system (e.g. on a television, video display, projected on a screen, such as a movie) or experienced as a live performance. The presentation can be passive, where the audience experiences the presentation from a stationary location (e.g., seated in a theater or in front of a television or video screen) or the presentation can be interactive where the audience is participating in some form of activity (e.g., live roller coaster ride, simulated roller coaster ride, an interactive session via the internet, a focus group). The data collected is processed in accordance with the invention in order to determine a measure of intensity, synchrony and engagement of the audience. The measure of intensity, synchrony and engagement for a population sample can further be used to predict the level of intensity, synchrony and engagement of the population. In the context of this disclosure, the population sample can be based on the measure of responses of a plurality of individuals to the same presentation (at the same time or different times) or multiple measures of responses of a single individual exposed to the same presentation multiple times.

In accordance with the present invention, a measure of the intensity of the response to the presentation over the period of exposure to the presentation and a measure of the synchrony of the response to the presentation over the period of exposure to the presentation can be determined from the biologically based responses. Further, the period of exposure can be divided into time slots or windows of a variety of durations (fixed or varying), or event based units with a corresponding response value determined for and associated with each time slot or event window. The measure of intensity can include measuring the change, from a base level, of a biologically based response to the presentation, aggregated across two or more biological measures and aggregated across the population or part of the population. Further, the response value can be determined as a function of the measured change and a set of predefined thresholds. The measure of synchrony can include determining a value indicative of the synchronized change or the correlation of the biologically based responses over the sample population. The measure of synchrony for a given time slot can be determined as a function of the inverse of the variance for the measured biologically based responses of the sample population for a common time slot. The measure of engagement can be determined by combining the measure of intensity and the measure of synchrony on a time slot by time slot basis. The measures of intensity and synchrony can be evenly or unevenly weighted in determining the measure of engagement.

The system can include three time-locked or synchronized sources of data: 1) a media presentation device or some other apparatus or forum for presenting the sensory stimulus or series of stimuli, 2) a response monitoring device for the collection of a plurality of biological responses to the presentation, and 3) an eye-tracking system and/or video camera to determine the location and duration of pupil fixation plus facial responses. Additional video cameras can be used to determine the proximity of the individual and/or audience to the media device and the specific elements of the presentation being experienced. The response monitoring device and the eye-tracking system and/or video camera can be time-locked or synchronized with the sensory stimulus so that the monitoring device and the eye-tracking system and/or video camera can consistently record the biological responses that correspond to the same portions of the presentation. The system sensor package can include, but is not limited to, a measure of skin conductivity, heart rate, heart rate variability, vagal tone, respiration, body movement, measures of facial muscle movement/expression, eye-tracking and other biologically based signals such as body temperature, near body temperature, facial and body thermography imaging, facial EMG, EEG, fMRI and the like. The presentation content can include, but is not limited to, passive and interactive television, radio, movies, internet, gaming, and print entertainment and educational materials as well as live social interaction, theatrical, experiential, and amusement presentations. The time-locked data sources can be connected to or transferred to a computerized data processor to automatically apply the described method of scoring resulting in a pattern (or map) of engagement per unit time (time slot), per event, or across the entire presentation.

The system can further use eye-tracking, directional audio and/or video, or other technology to isolate specific elements or moments of interest for further in-depth processing. In accordance with the invention, the system can track what content is being viewed, who is viewing the content and which biological responses of the audience correspond to the viewed content.

The system can provide an objective view of how an audience will respond to a presentation. The system can further include a database of biologically based audience responses, response patterns and audience engagement patterns and levels to a variety of historic media stimuli that, when combined with demographic and other data relevant to the test media content, allows for a prediction of the relative success of that content.

A method is described for calculating an index of time-locked engagement. The method involves aggregation of the biological responses of the sample audience. In order to aggregate the responses of a sample population or group of participants, it is desirable to process the data according to one or more of the following procedures:

1. Time-locking the individual data streams into time slots or windows; the biological response data can be divided into sequential blocks that are associated with specific time slots;
2. Determining and processing the data based upon individual baselines and individual variances; the biological response data can be normalized to compensated for varying responses of the individual members of the sample population and the sensing equipment used;
3. Determining and processing the peak and trough values for each time slot to compare with the individual baselines and variances and determining and processing the rate of change for each time slot of one or more biological responses;
4. Determining a standardized score per time slot for each biological measure;
5. Combining the standardized score per time slot across the sample population using one or more of the standardized scores for one or more of the biological measures to create a measure of intensity. Preferably, more than one biological measure is used with at least one biological measure being weighted differently than other biological measures, depending on the sample population and presentation or content;
6. Averaging the inverse of the residual variance of the rate of change per unit time of a subset of biological measures across the test audience to create a measure of synchrony with some biological measures being weighted differently than other biological measures depending on the test population and test content;
7. Combining the measure of intensity and the measure of synchrony to create an overall measure of engagement per unit time; Preferably, either the measure of intensity or the measure of synchrony can be weighted differently, depending on the sample population and the presentation or content;
8. Standardizing the resulting measure of engagement per time slot to a set number of individuals (sample population size) for comparison with other tests in other populations of various sizes.

In accordance with one embodiment of the system, a sample audience is presented with a sensory stimulus or piece of media content (live or pre-recorded) in a test theater that can last from a minimum of a few seconds to several hours. For the purposes of this invention, the sample audience can be a single individual who is monitored viewing the same content several times or a group of individuals. Monitoring of audiences can be done individually, in small groups, or in large groups simultaneously. The audience can be of a tightly defined demographic/psychographic profile or from a broadly defined demographic/pyschographic profile or a combination of the two. The system records the time-locked data streams, calculates the level of moment-to-moment engagement, and compares the pattern of engagement to a database of similar media content. The system is further able to use eye-tracking or other technology to isolate specific elements or moments of interest for further in-depth processing. In accordance with the invention, the system can track what content is being viewed, who is viewing the content and which biological responses of the audience correspond to the viewed content. Thus, for a given piece of stimulus content, the biological responses can be connected with the portion of the content that elicited the response and the data from more than one sample audience or a subset of sample audiences gathered at different times and places can be aggregated.

In accordance with another embodiment, participating members of a household can control their media choice and usage throughout the course of their day while they wear a sensor device (for example, a special article of clothing, a bracelet or other device) that measures some combination of biological responses as they watch television, listen to music, or use the internet. In this embodiment, the in-home sensing device communicates with an in-home computer or set top box (STB) that determines the nature and timing of the media content the participant has chosen as well as identifying information about the participant. The system would include a technology that could determine the distance from the media stimulus such as distance measurement via technologies like infrared, global positioning satellite, radar or through the acquisition of a signal between two objects, such as the television or computer and participant using technologies with a known range of operation (e.g., WiFi, Zigbee, RFID, or Bluetooth) and/or the direction of the participant eye-gaze (e.g., using eye-tracking technology). In a variant of this embodiment, the STB or computer can prevent activation of home media devices unless the sensor device was activated to ensure compliance. In another variant of this embodiment, test presentation content and/or broadcast/cable presentation content can be "pushed" to the participant that "matches" a desired demographic/psychographic profile or pre-determined level or pattern of engagement. As in prior embodiments, the system can record the time-locked data streams, calculate the moment-to-moment level of engagement relative to that person, and compare the pattern of engagement to a database of similar individual experiences.

In accordance with another embodiment, the presentation that provides that sensory stimulus can be a live person or persons or activity. This live person or persons may include, but is not limited to, live focus group interactions, live presentations to a jury during a pre-trial or mock-trial, an interview-interviewee interaction, a teacher to a student or group of students, a patient-doctor interaction, a dating interaction or some other social interaction. The live activity can be an activity, for example, riding on a rollercoaster, in a boat or in a car. The system can record the time-locked data streams, calculate the moment-to-moment level of engagement, and similar to the other embodiments, compare the pattern of engagement to a database of similar social interactions to make an estimate of the response pattern relative to other response patterns for that type of social interaction.

The present invention relates to a system and method for use in the field of audience measurement. A system is described for recording the biologically based audience responses to a live or recorded, passive or interactive audio, visual or audio-visual presentation that provides a sensory stimulating experience to members of the audience. A method is described for using the biologically based audience responses to calculate a pattern of intensity, synchrony and engagement measures. The method can involve the conversion of the biological responses of a plurality of participants into standardized scores per unit time, per event, or aggregated over time/events that can be aggregated across the sample population audience. The system determine the intensity and synchrony of the moment-to-moment and overall experience for the sample population audience. The standardized intensity and synchrony scores can be combined to create an overall measure of audience engagement. The measure of engagement represents an objective measure of the experience of a defined audience segment based on a plurality of biologically based measures.

The measure of engagement is determined from two components which are determined from the plurality of biologically based measures. The first component is the measure of intensity, which reflects the intensity of the biologically based responses to a plurality of defined portions of the presentation (represented by time slots or events). The second component is the measure of synchrony, which reflects the correlation or coincidence of the change in biologically based responses (how many people had the same or similar responses to the same content) in the sample population for a plurality of defined portions of the presentation (represented by time slots or events)

The system can further integrate time-locked eye-tracking and other video monitoring technology with the measure of engagement to identify specific elements of the sensory stimulus that are triggering the responses. The system can also use the measure of engagement to anticipate the relative success or failure of the test stimulus via predictive models using a database of historic patterns of engagement for similar test stimuli in similar audiences.

FIG. 1 shows a schematic diagram of an embodiment of the system according to the invention. The presentation is presented to the audience 12 via a display device 10, such as a video display screen or other commercially available technology for presenting the presentation to the test or sample audience 12. The presentation can include, but is not limited to, passive and interactive television, radio, movies, internet, gaming, and print entertainment and educational materials. The display device 10 can include but is not limited to a television, movie screen, a desk-top, hand-held or wearable computer device, gaming console, home or portable music device or any other device for the presentation of passive or interactive audio, visual or audio-visual presentation. For the purposes of this invention, the test audience 12 can be a single individual who is monitored viewing the same content several times, or any small or large group defined by any number of parameters (e.g., demographics, level of interest, physiological or psychological profile). The test audience can be monitored using a biological monitoring system 12a for the collection of a plurality of biological responses time-locked to each other and the test stimulus. The system can include a focus and/or facial monitoring system 14 (e.g., eye-tracking system, or a digital video camera) for the collection of data on the behavior, facial response and/or precise focus of the audience. The three data-sources (media stimulus, biological response data, and focus data) can be synchronized or time-locked and/or event-locked to each other whereby the response data collected is associated with a portion of the presentation and sent to a computer data processing device 16. The computer data processing device can be a general purpose computer or personal computer with a processor, memory and software for processing the biological response data and generating the intensity, synchrony and engagement values. The three data sources can be time-locked or synchronized externally or in the data processor 16 by a variety of means including but not limited to starting them all at the same time, or by providing a common event marker that allows the each system (in data processor 16) collecting the data from the three data sources to synchronize their clocks/event timers or simply synchronizing the clocks in each of the systems or use a common clock. The data processing device 16 can run software that includes the scoring algorithm to calculate the moment-to-moment, event-to-event or total level of engagement and compares it to a database of other audience responses to the same or similar test presentations and delivers the results to a user-interface 18. The user interface 18 can be provided on a desktop or portable computer or a computer terminal that accesses data processor 16. The user interface 16 can be a web based user interface or provided by a dedicated client running on the desktop or portable computer or computer terminal. The results can be interpreted and collected into a printed or electronic report 20 for distribution. The response data can be associated with the portion of the presentation that was displayed when the response was measured. Alternatively, the response data can be associated with an earlier portion of the presentation that is presumed to have caused the response based on a determined delay.

The monitoring device 12A for measuring biological responses can be any of a number of commercially available or other sensors known in the prior art for measuring such responses. In accordance with the current invention, the least invasive and obtrusive sensors with the most comfortable form factor should be chosen to minimize disruption of the experience. Preferably, the sensors should allow participants to experience the test stimulus "as if" they were not being monitored at all. Form factors include but are not limited to wearable devices such as smart garments, watches, and headgear. Many devices are available and known to collect measures of the autonomic nervous system, facial musculature, motion and position, vocal features, eye-movements, respiratory states, and brain waves. Multiple combinations of sensors can be used depending on the sensory stimulus, population, and location of the monitoring.

An example of a method according to the invention for determining a measure of engagement can include the following Intensity Score Each measure of intensity can be associated with point in time or a window or bin of time or event marker within the exposure period. This association can be accomplished using many methods. Preferably, the methodology for associating a measure of intensity with a point in time or a window of time within the exposure period is the same or similar for each measure of engagement determined in a population sample. For example, in one method, a given measure of intensity associated with a change in a biologically based response is assigned to the time slot or window that corresponds to where one half the rise time of that response occurs.

For example, the input to the data processor 16 can be an N by M data matrix where N is the number of subjects and M is the number of time points during which the biological response is recorded. The data processor 16 can include one or more software modules which receive the biological response data and generate the N by M matrix that is used in subsequent processing steps. The data processor 16 can include an intensity processing module which receives the N by M matrix of biological response data, calculates one or more standardized scores for each biological response measured and each time slot. The output can be a total integer score of the intensity of response across subjects in time windows of W seconds width (this is a variable parameter that depends on the presentation). The fractional rise time parameter (f-rise) can be used to estimate the related time window or slot in which the response occurs. For example, if a change in a biologically based response occurs over three time slots or windows, W1, W2, W3, and one half the rise-time of the response occurred during window W2, the measure of intensity for the change in response would be associated with window W2. Alternatively, the measure of intensity could be associated with the window that contained the peak (i.e. window W3) or the window that contained the trough (i.e. window W1). In addition, a fractional standard deviation parameter (f-std) can be used to estimate the degree of the change in response from baseline.

As a result, for each person, a response map can be determined as a set of intensity values associated with each time (or event) window during which each person was exposed to the presentation. The measure of intensity for the sample population can be determined by adding the measure of intensity associated with the same time window for each person exposed to the presentation. The result is a response time line that is the aggregate of the population sample. The response patterns for two or more biologically based responses (e.g. skin conductivity, heart rate, respiration rate, motion, etc.) can be combined (evenly or unevenly weighted) in a time window by time window basis to determine an overall intensity score or intensity time line. The aggregate can be normalized for a population size, for example 10 or 25 people.

In accordance with the invention, the response map or pattern can be used to evaluate radio, print and audio-visual advertisements (for both television and the Internet), television shows and movies. In one embodiment, a population sample can be exposed to one or more known successful advertisements (TV shows, movies, or websites) and then the same or a different population sample can be exposed to a new advertisement (TV show, movie, or website). Where the response pattern is similar to the response pattern to one or more known successful advertisements (TV shows, movies, or websites) it would be expected that the new advertisement (TV show, movie, or website) would also be successful. Further, a database of response patterns for different types of stimuli (advertisements, TV shows, movies, websites, etc.) could be maintained and analyzed to determine the attributes of a successful advertisement, TV show, movie, or website.

In accordance with the invention, the data processor 16 can include a synchrony processing module which receives the N by M matrix of biological response data, calculates the inverse variance of the rate of change of one or more biological measures across at least a portion of the sample population and determines a standardized value representative of the synchrony for a given time slot. The data processor 16 can determine the synchrony of a given biological response by evaluating the slope of the response in a given time window or event window over the period of exposure for each person in the population sample. For each time window, a slope value can be assigned based on the value of the slope, for example, the greater the slope the greater the slope value. The slope value for each corresponding time window or event window of each person of the population sample can be processed to determine a measure of the variance over the population sample for each time window or event window. For example, the mean and standard deviation of the slope value of the population sample for each time window or event window can be determined and used to further determine the residual variance. The residual variance can be further normalized and used to produce a response pattern that indicates the time-locked synchrony of the response of the population sample to the stimulus.

Similarly, the synchrony response map or pattern can be used to evaluate radio, print and audio-visual advertisements (for both television and the Internet), television shows and movies. Further, the stimuli described can be evaluated using both the intensity response pattern and the synchrony response pattern.

The intensity score can be calculated according to the following steps. Step 1: Following a noise reduction process for each input channel, for each participant, the distribution of amplitudes of responses including the mean ($\mu$) and standard deviation ($\sigma$) of responses is calculated over some baseline period (this is a variable parameter that depends on the stimulus). Step 2: For each participant, the location and timing of the trough and peak amplitude of each response is estimated and the difference between each peak and trough (the amplitude of response) is calculated. Step 3: The values so determined are used to establish a score for each individual response thus: score 0 if the amplitude is less than the baseline $\mu$ for that channel, score 1 for a response if the amplitude is between $\mu$ and $\mu+f-(\sigma)$, and score 2 for a response if the amplitude is greater than $\mu+f-(\sigma)$. Step 4: Each response score for each participant is assigned to a sequential bin of variable length time-locked to the media stimulus by locating the time of the f-rise. Step 5: The sum of all the binned response scores across all participants is calculated for each biological sensor. The score is normalized depending on the number of sensors collected (being equal for each test) and the number of participants (being unequal for each test). The score thus created is the intensity score per unit time or per time slot.

Depending on the sensors used and the presentation being experienced, not all channels will be added to the intensity score. For example, certain forms of respiration (such as a sigh indicative of boredom) or motion (taking a drink or looking at a watch) may actually be subtracted from the intensity score. In addition, alternative versions of the intensity measure may be used for presentations with differing goals. For example, when testing a horror movie, sensors such as skin conductance may be weighted more heavily in the calculation because the goal of the content is to generate arousal while testing a comedy, which is meant to elicit laughter might use stronger weighting towards the respiratory response.

Synchrony Score

Synchrony is a measure of the rate of change of a response by a the audience (plural members of the sample population) to a portion of the stimulus or presentation. The audience can be exposed to the stimulus or presentation over a period of time or through a sequence of steps or events. The period of exposure can be divided into windows or portions or events that correspond to elements or events that make up the stimulus or presentation. For example, the synchrony of the response can be determined as a function of the rate of change of a biologically based response to a portion of the stimulus or an event during the presentation by a plurality of audience members or the population sample.

In accordance with the invention, the input to the data processor 16 can be an N by M data matrix where N is the number of subjects and M is the number of time points during which the biological response is recorded. The data processor 16 can include a synchrony processing module which receives the N by M matrix of biological response data, calculates an inverse variance across the matrix values and determines one or more standardized scores for each biological response measured and each time slot. The output will be a total integer score of the synchrony of response across subjects in time windows of W seconds width (this is a variable parameter that depends on the stimulus). In accordance with the invention, the synchrony of a given response is determined by evaluating the rate of change of the response in a given time window or slot over the period of exposure for each participant in the test audience.

The synchrony score can be calculated according to the following steps. Step 1: Following a noise reduction process for each input channel, create a sliding window of variable width moving forward in time increments that are smaller than the window size. Step 2: In each window, for each participant, compute the first derivative of one or more of the response endpoints. Step 3: Across all participants, calculate the mean ($\mu$) and the standard deviation ($\sigma$) of the rate of change in each window. Step 4: From the above compute a score=$-\ln|\sigma-\mu|$. Step 5: Scale the resultant score so that all numbers are between 0 and 100. Step 6: Compute the windowed scores commensurate with the intensity score windows by averaging the sliding scores into sequential windows of 5 variable length time-locked to the media stimulus. The score thus created is the synchrony score per unit time or per time slot.

Engagement Score

The intensity and synchrony scores may be added together to compute the moment-to-moment engagement score per unit time or per time slot. Depending on the nature of the test presentation and the test audience, one of the intensity and synchrony scores may be weighted relative to other. For example, for some tests it may be preferred to identify the most extreme responses and thus intensity would be weighted more heavily. Alternatively, different functions can be used to determine different forms of the engagement score. For example, multiplying intensity by synchrony creates exaggerated graphs more readable and usable in some situations such as when evaluating multiple hours of trial testimony, it may be useful to identify the most extreme examples of engagement.

Figure 4A:
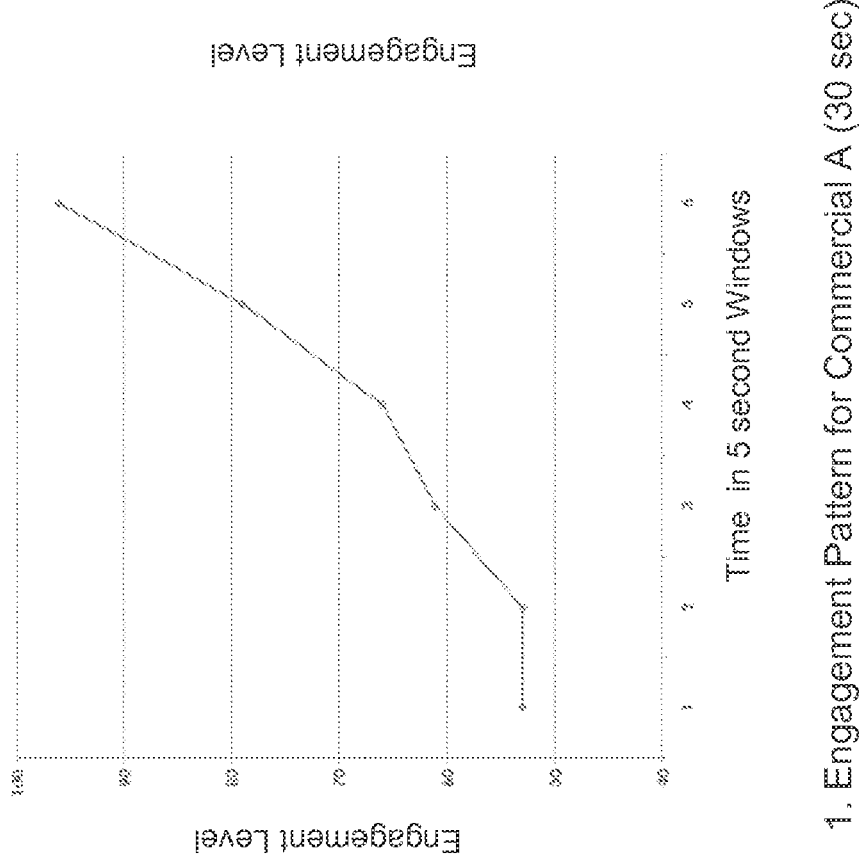
FIG. 4A shows an engagement pattern for a 30 second commercial according to the invention and FIG. 4B shows an engagement pattern for a 60 second commercial according to the invention.
Figure 4B:
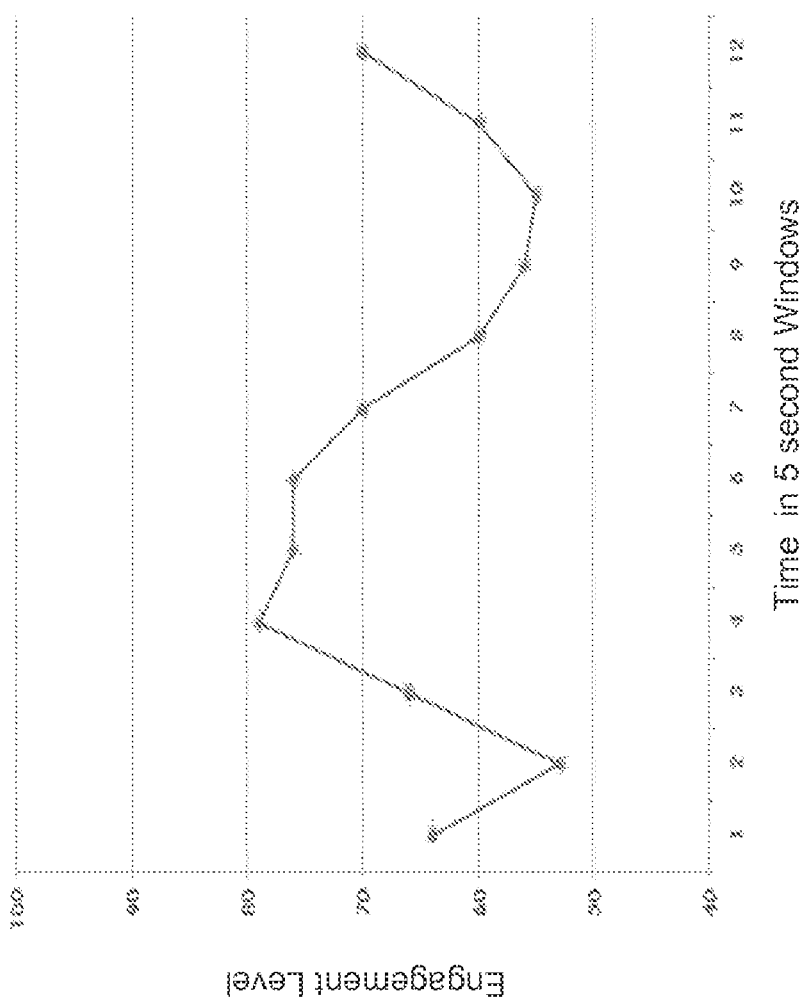

FIGS. 4A and 4B show two examples of a measure of engagement determined in accordance with the invention. The diagrams were generated from a sample population audience of 20 males. FIG. 4A shows a measure or pattern of engagement for a 30 second commercial, the time period is divided into six 5 second time slots and an engagement value from 40 to 100 is determined for each time slot. As the diagram in FIG. 4A shows, the pattern of engagement increases with time. FIG. 4B shows a measure or pattern of engagement for a 60 second commercial, the time period is divided into twelve 5 second time slots and an engagement value from 40 to 100 is determined for each time slot. The commercial of FIG. 4A had three times the number of viewers who did not change the channel as compared to the commercial of FIG. 4B.

Predictive Modeling

The system can further include a database of audience engagement to a variety of historic media or other relevant stimuli or experiences that when combined with demographic/psychographic profiles and other data relevant to the test content that allows for a prediction of the relative success of that content in a similar population. After testing an audience, various forms of the output from the described method can be used to estimate the likelihood of the success of the sensory stimulus in achieving its goal. The statistical analyses for creating predictive models can include, but are not limited to, variables related to the product or the content itself, the price of sale or cost of production of the product or content, the place of purchase or medium of experience, the cost of promotion, and/or the characteristics of the audience. For example, factors included in a model for the television industry may include but are not limited to: a) number of viewers per time slot, b) ratings of the lead-in show, c) ratings of the following show, d) mean ratings for the type of show, e) lead actor/actress popularity rating, f) time of year, g) advertising revenue, h) promotional budget for the show, and/or i) popularity of the network. Other factors may include but are not limited to characteristics of the target audience such as: a) reported liking of the show, b) psychographic characteristics (e.g., introversion vs. extroversion), c) demographic characteristics, and/or d) ability to recall or recognize elements of the show. Indicators of success can include but are not limited to how likely a population with similar characteristics is to watch the television show outside of a testing theater and/or how likely a population with similar characteristics will remember and/or purchase the products being advertised. Preferably, the more people tested (the larger the sample population) and the better characterized the population, the more likely that the model can be an accurate predictor of a larger population response. The preferred predictor model can include, but is not limited to, any of the following statistical methods: a) mixed media models, b) traditional multivariate analyses, c) hierarchical linear modeling, d) machine learning, e) regression analyses, f) Bayesian shrinkage estimators, and/or g) cluster and factor analyses.

Figure 2A:
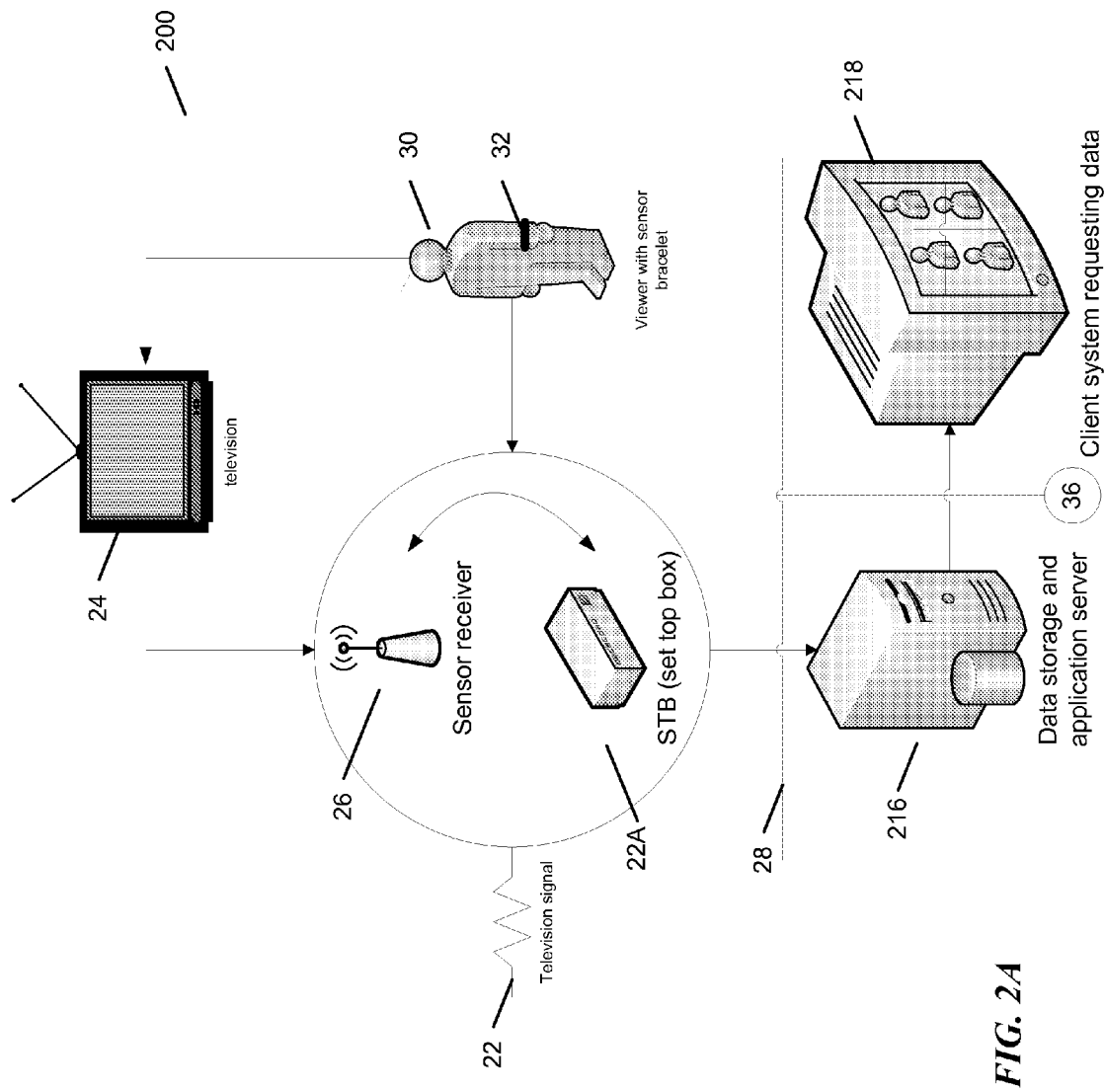
FIG. 2A is a schematic diagram of a second embodiment of the system according to the invention for audience measurement in the home.

FIG. 2A shows a schematic diagram 200 of a second embodiment of the system according to the invention. In this embodiment, the media stimulus is presented via commercially available video signals 22, such as the cable TV signal and plugs into the STB 22A. In turn, the STB 22A enables programs to be displayed on the media device 24 such as a TV monitor, computer, stereo, etc. In this system, a participant 30 in viewing distance wearing a wireless biological sensor package in an unobtrusive form factor like a bracelet 32 interacts with the media device. As long as that person is in basic viewing distance, the sensor receiver 26, which can be a separate unit or built into the STB 22, will receive information about that participant. The system 200 can time-stamp the biological responses along with the unique identifier of that participant. This data can be time-stamped against the programming currently being played by the participant. This information can be sent back to a central database 216 via a transmission network 28 such as an internet connection, pager, or cellular network. The data can be combined with demographic, household, family, community, location and any other type of information potentially relevant to the end-user and processed by software using the scoring algorithm described in this application to calculate the moment-to-moment pattern of engagement and compared to a database of other audience responses to the same or similar media test stimulus 36 and processed using the engagement score and/or predictive models as described above and delivered to a user-interface (11) to generate reports for distribution.

Figure 2B:
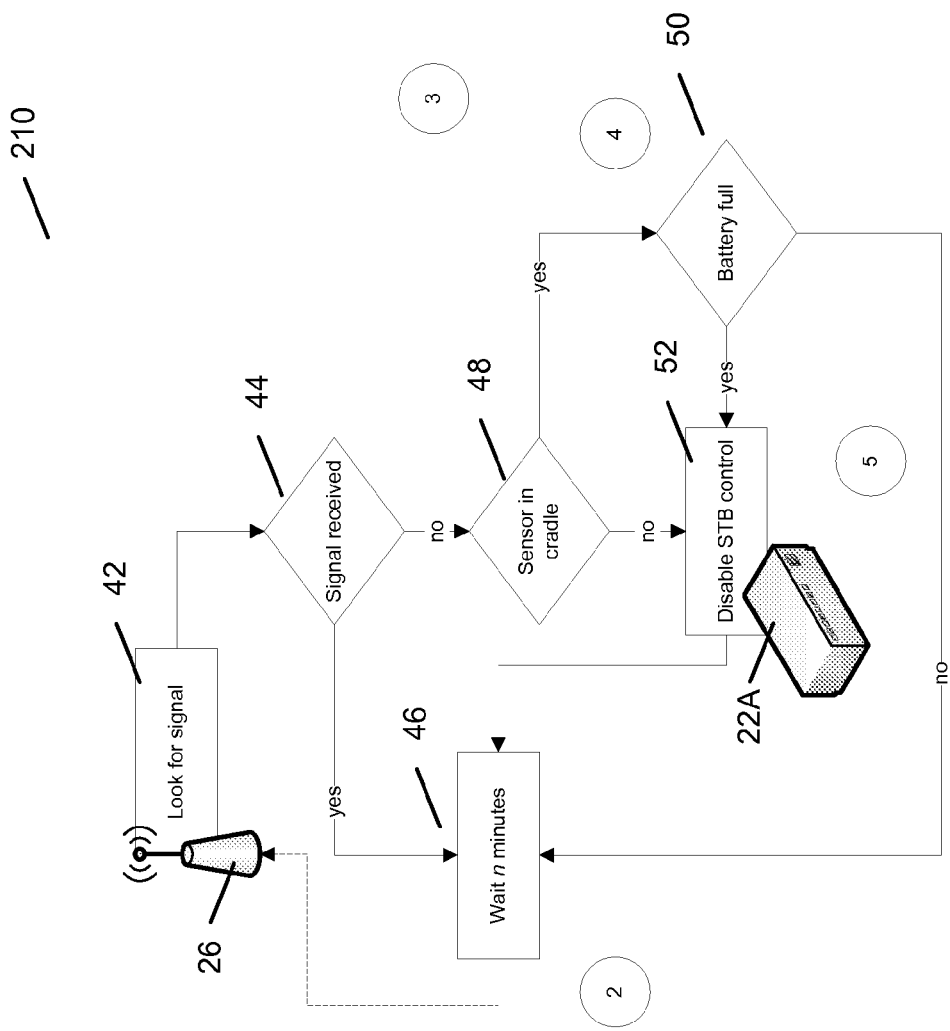
FIG. 2B is a flow diagram of the in-home compliance algorithm for the second embodiment.

FIG. 2B shows a flow diagram 210 of the in-home compliance algorithm to improve usage of the in-home embodiment of this invention. In a household where this system can be set up, compliance can be dealt with by controlling the ability to change programming on the media device being used. The STB 22A can be programmed such that it will not function (partially or completely) if the sensor device is not being worn and is not active. If the sensors are being worn or charging, the STB can be programmed to work. If, however, the sensors are not being worn and are fully charged, the STB can be programmed not to respond fully or partially. In a partial functionality mode, only certain stations may be available, for example, public access and emergency stations. The flow chart 210 of the operation involves a receiver 26 that checks 44 to see if it is getting a signal 42 from the sensor or sensors, which is only possible if the sensor is activated and is being worn. If the receiver is getting a signal, it waits a set amount of time before starting over 46. If it does not receive a signal, the system checks whether a sensor device is being charged in the attached cradle 48. If so and the battery is not full, it also waits a set interval before checking again 50. If, however, the sensor is not active, not charging or fully charged and not being used, the STB can become inactive until the next check shows a change 52.

FIG. 2C shows one aspect of the in-home system, i.e., its ability to identify who in a given household is actually watching. The wireless technology involved in connecting the sensor with the receiver sends out a unique identifier. This identifier will be related to the data sent out in order to identify the source of the biometric data and link it to the current media stimulus. Anyone wearing a sensor but not in the defined wireless range from the receiver will not have their information tracked while outside of that range. The system will wait for a period time 68 if no wireless signal is received. If they are in the range of another receiver 62 (and STB 26) and the signal is received 62, however, their information can be tracked by that system. The flow chart 220 involves a wireless technology 26 (e.g., Bluetooth) that is used to connect the sensor device to the receiver or STB 22A. Wireless communications can be used to establish a connection 66 and transfer data between the receiver (not shown) and the STB 22A as well as to transfer data needed to determine compliance above. Once a participant is identified, information regarding that participant is collected and sent 70 to the database (DB) and processed as above 74 to generate reports for distribution.

Figure 3:
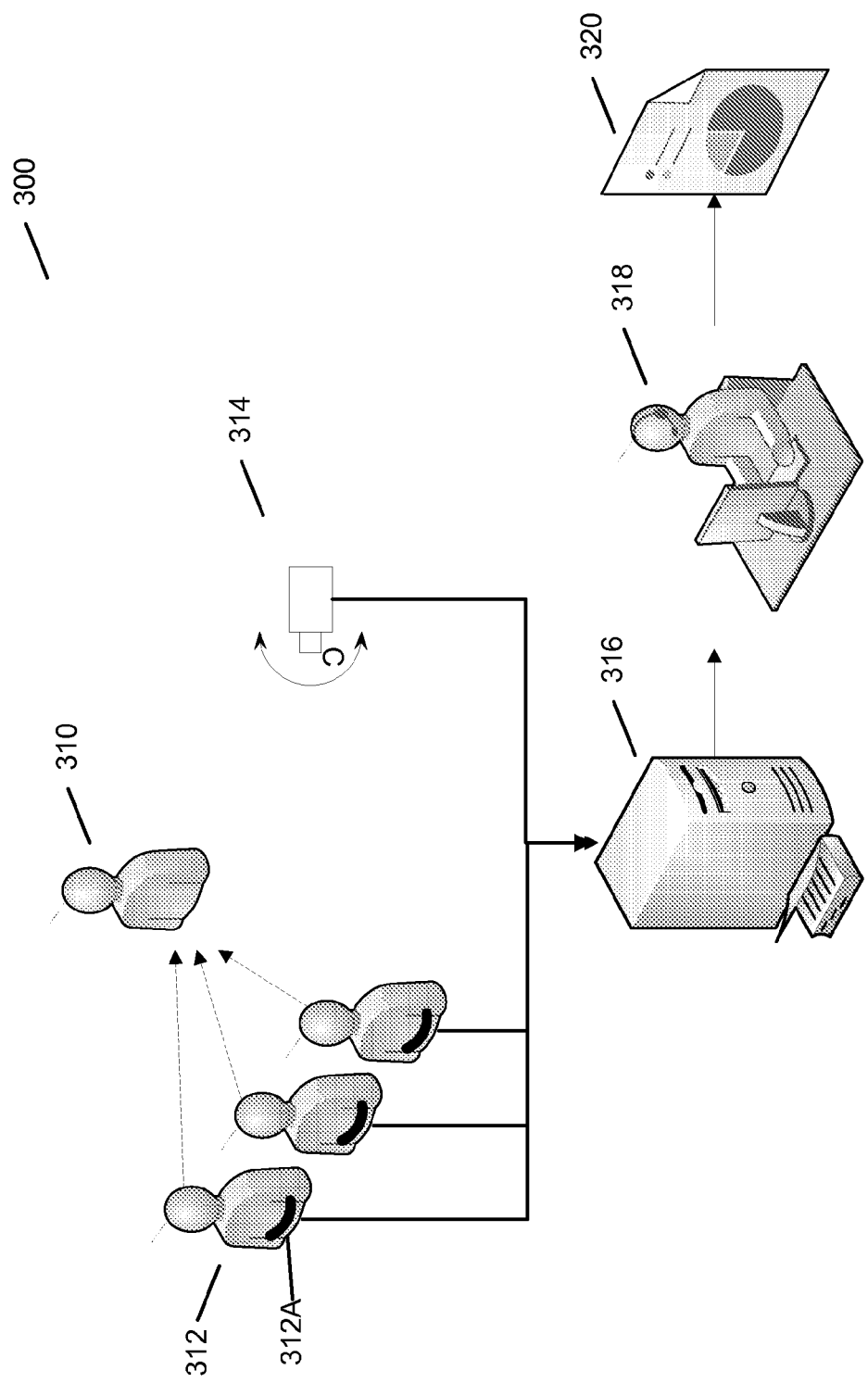
FIG. 3 is a schematic diagram of the third embodiment of the system according to the invention for monitoring levels of engagement during social interaction.

FIG. 3 shows a schematic diagram of the third embodiment of the system 300 according to the invention. In this embodiment, the sensory stimulus can be a live person 310 and the system and method of the invention can be applied to a social interaction that can include, but is not limited to live focus group interactions, live presentations to a jury during a pre-trial or mock-trial, an interview-interviewee interaction, a teacher to a student or group of students, a patient-doctor interaction, a dating interaction or some other social interaction. The social interaction can be monitored for each individual 312 participants biologically based responses time-locked to each other using a biological monitoring system 312A. An optional audio-video camera or other monitoring device can be focused on the audience 314 to monitor facial responses and/or eye-tracking fixation duration and location. The data-sources can be time-locked to each other and sent to a computer data processing device 316. The data processing device 316 can run software that includes the scoring algorithm to calculate the moment-to-moment pattern of engagement and compare it to a database of other audience responses to the same or similar media test stimulus and deliver the results to a user-interface 318. The results can be processed in a predictor model as described above and interpreted and collected into a report 320 for distribution.

The algorithm can be either presented alone or plugged into a model of the relevant industry. Taking television pilot testing as an example, the model can include factors such as:
1. Typical viewers per timeslot
2. The ratings of the lead-in show
3. The ratings of the following show
4. Average ratings per genre
5. Actor popularity—QRating
6. Ratings of shows competing in the timeslot
7. Time of year
8. Promotional budget for the show
9. Demographics of the network An example from advertising can include all of these variables but may add:
1. Flighting/repetition
2. Length of segment
3. Audience target
4. Demographics of the containing program Other embodiments are within the scope and spirit of the invention. For example, due to the nature of the scoring algorithm, functions described above can be implemented and/or automated using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

The invention claimed is:

1. A method of determining a measure of engagement of an audience for a presentation providing a sensory stimulus comprising:
   exposing the audience to the presentation over a period of time, wherein said period of time is divided into two or more time slots;
   providing a plurality of sensors, wherein the plurality of sensors measure a plurality of biologically based responses to said presentation for each member of the audience;
   providing a computer processing system adapted for receiving data relating to the presentation and data from the plurality of sensors;
   determining for each time slot at least one intensity value as a function of at least one of the measured biologically based responses;
   determining for each time slot at least one synchrony value as a function of a rate of change of at least one of the measured biologically based responses, wherein the synchrony value represents a number of audience members with the same or similar biologically based response for the at least one measured biologically based response;
   determining for each time slot at least one engagement value as a function of at least one of said intensity values and at least one synchrony value; and
   comparing the at least one engagement value to a database comprising stored engagement values to determine at least one indicator of success.

2. A method according to claim 1, wherein the step of comparing comprises:
   indicating that the presentation is similar to a second presentation based on the comparison.

3. A method according to claim 1 wherein said biologically based responses are chosen from a group of responses including heart rate, skin conductance, respiration rate, respiration state, motion, and eye tracking.

4. A method according to claim 1 wherein determining said at least one intensity value includes determining a standardized score as a function of at least one of a peak value, a trough value, a median value, an average value and a rate of change value of at least one of the biologically based responses.

5. A method according to claim 1 wherein determining said at least one synchrony value includes determining a variance of a rate of change value of at least one of the biologically based responses over at least a portion of the audience.

6. A computerized system for determining measure of engagement of an audience for a presentation providing a sensory stimulus, the system comprising:
a plurality of sensors, each adapted for measuring a biologically based response to the presentation over a period; the time period being divided into two or more time slots;
a computer processing system adapted for receiving data relating to the presentation and data from the plurality of sensors providing a measure of at least one biologically based response to the presentation;
an intensity processing module adapted for determining, for each time slot, at least one intensity value as a function of at least one of the measured biologically based responses;
a synchrony processing module adapted for determining, for each time slot, at least one synchrony value as a function of at least one of the measured biologically based responses, wherein the synchrony value represents a number of audience members having the same or similar biologically based response for the at least one measured biologically based response;
an engagement processing module adapted for determining, for each time slot, at least one engagement value as a function of said at least one intensity value and said at least one synchrony value; and
a database of stored engagement values, wherein the at least one engagement value is compared to the stored engagement value to determine similarity.

7. A system according to claim 6, wherein the database further comprises an indicator adapted for indicating that the presentation is similar to at least one other presentation based on a comparison of the at least one engagement values to the stored engagement values.

8. A system according to claim 6 wherein said biologically based responses are chosen from a group of responses including heart rate, skin conductance, respiration rate, respiration state, motion, and eye tracking.

9. A system according to claim 6 wherein said intensity processing module is adapted for determining the intensity value as a function of a standardized score and the standardized score is determined as a function of at least one of a peak value, a trough value, a median value, an average value and a rate of change value of at least one of the biologically based responses.

10. A system according to claim 6 wherein said synchrony processing module is adapted for determining the synchrony value as a function of a variance of a rate of change value of at least one of the biologically based responses over at least a portion of the audience.

11. The method of claim 1, wherein the step of determining for each time slot at least one intensity value comprises determining a first intensity value as a function of a first measured biologically based response and a second intensity value as a function of a second measured biologically based response.

12. The method of claim 1, wherein the step of determining for each time slot at least one intensity value comprises determining a first intensity value as a function of a first measured biologically based response and a second intensity value as a function of a second measured biologically based response.

13. The method of claim 11, wherein the first measured biologically based response comprises heart rate and the second measured biologically based response comprises skin conductance.

14. The method of claim 12, wherein the first measured biologically based response comprises heart rate and the second measured biologically based response comprises skin conductance.

15. The method of claim 1, wherein the plurality of biologically based responses are selected from the group consisting of heart rate, heart rate variability, skin conductance, vagal tone, respiration, body movement, facial muscle movement, facial expression, eye tracking, body temperature, near body temperature, facial thermography imaging, body thermography imaging, facial EMG, EEG, and fMRI.

16. The system of claim 6, wherein the synchrony processing module is capable of determining, for each time slot, at least two synchrony values for at least two measured biologically based responses.

17. The system of claim 16, wherein the intensity processing module is capable of determining, for each time slot, at least two intensity values for the at least two measured biologically based responses.

18. The system of claim 17, wherein the at least two measured biologically based responses are selected from the group consisting of heart rate, heart rate variability, skin conductance, vagal tone, respiration, body movement, facial muscle movement, facial expression, eye tracking, body temperature, near body temperature, facial thermography imaging, body thermography imaging, facial EMG, EEG, and fMRI.

19. The system of claim 17, wherein the at least two measured biologically based responses are heart rate and skin conductance.

* * * * *